(12) United States Patent
Gebert et al.

(10) Patent No.: US 6,457,345 B1
(45) Date of Patent: *Oct. 1, 2002

(54) REPEATED IMPACT APPARATUS AND METHOD FOR CHARACTERIZING GRANULE STRENGTH

(75) Inventors: Mark S. Gebert, Pacifica, CA (US); Ramanan Pitchumani, Delft (NL); Willem J. Beekman, Delft (NL); Gabriel M. H. Meesters, Delft (NL); Brian Scarlett, Den Haag (NL)

(73) Assignee: Genencor International, Inc., Palo Alto, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 09/611,631

(22) Filed: Jul. 7, 2000

Related U.S. Application Data

(60) Continuation-in-part of application No. 09/382,450, filed on Aug. 25, 1999, now Pat. No. 6,173,601, which is a division of application No. 08/681,250, filed on Jul. 22, 1996, now Pat. No. 6,035,716.

(51) Int. Cl.[7] ................................. G01N 3/56
(52) U.S. Cl. ............................. 73/7; 73/592
(58) Field of Search ............... 73/573, 664, 570, 73/572, 571, 662, 663, 579, 578, 577, 7, 12, 87, 866

(56) References Cited

U.S. PATENT DOCUMENTS

| | | | |
|---|---|---|---|
| 3,282,084 A | 11/1966 | Banks | 73/579 |
| 3,511,078 A | 5/1970 | Rajkai | 73/432 |
| 3,636,772 A | 1/1972 | Bennett | 73/7 |
| 3,766,776 A | 10/1973 | Williams | 73/78 |
| 4,166,527 A * | 9/1979 | Beezer | 74/24 |
| 4,685,326 A | 8/1987 | Peterson | 73/580 |
| 4,703,647 A | 11/1987 | Eckhoff et al. | 73/81 |
| 5,140,857 A | 8/1992 | Reid | 73/7 |
| 5,152,401 A | 10/1992 | Affeldt, Jr. et al. | 73/279 |
| 5,212,994 A | 5/1993 | Von Aifthan et al. | 73/866 |
| 6,035,716 A | 3/2000 | Beekman et al. | 73/579 |
| 6,173,601 B1 | 1/2001 | Beekman et al. | 73/7 |

FOREIGN PATENT DOCUMENTS

| | | | |
|---|---|---|---|
| GB | 2 181 559 A | 4/1987 | |
| RU | 1213376 | 2/1986 | 73/579 |

* cited by examiner

Primary Examiner—Helen Kwok
(74) Attorney, Agent, or Firm—Kilyk & Bowersox, P.L.L.C.

(57) ABSTRACT

The present invention provides methods and devices for measuring granule impact strength and granule attrition rates by vibrating a small container of granules at a well-controlled amplitude in order to inflict reproducible damage to the granules. Damage to the granules is measured as a function of time and amplitude and attrition rates are measured in terms of dust generate per number of collisions versus mass of the granules. The measurements obtained yield a highly reproducible means for characterizing granule attrition, attrition rates, and fragmentation.

27 Claims, 5 Drawing Sheets

REPEATED IMPACT APPARATUS AND METHOD FOR CHARACTERIZING GRANULE STRENGTH

CROSS-REFERENCE TO RELATED APPLICATIONS

This application is a continuation-in-part of U.S. patent application Ser. No. 0 09/382,450 filed Aug. 25, 1999, which is a divisional of U.S. patent application Ser. No. 08/681,250, filed Jul. 22, 1996, now U.S. Pat. No. 6,035,716, all of which are incorporated herein in their entireties by reference.

FIELD OF THE INVENTION

The present invention relates to a method and device for measuring the impact strength for individual granules over a wide distribution and for aspherical sizes.

BACKGROUND OF THE INVENTION

In any manufacturing involving the use or movement of particulate materials, some breakdown or attrition of the particles is inevitable and has been reported in a wide range of processes and industries. For example, it has significance for those applications where it is desirable for particles to remain in a process almost indefinitely. The effects of attrition can be loss of product by removal of undersize particles, the need for recycling lost product, and the requirement for additional filtration. Another effect can be to limit the useful life of catalyst or enzyme particles.

Many products in the pharmaceutical industry, for example, are agglomerated granules which can suffer attrition during processing and also, if bulk packed, during shipment and use. Dust release into the atmosphere may be a hazard, but its release is also undesirable because of the high value of many of the products.

Attrition has a number of different effects, the relative importance of which is dependent upon the commercial or technical application. Properties of particulate materials change as a result of attrition. Loss of material occurs due to the change of particle sizes to smaller ones which are unacceptable to the particular process and which are removed from the process by accident or design in cyclones, filters, or precipitators. Wear of contaminant systems results from the impact of particles with the walls of the container or duct, and contamination of the process particles by debris from wear of the containment system may be significant in some applications. Even an explosion can be caused if a build-up of fine material is allowed to occur.

Several conventional methods for testing the mechanical strength of industrial catalysts which are used in fluid beds are reported in C. R. Bemrose and J. Bridgwater, A Review of Attrition and Attrition Test Methods, *Powder Technology*, 49 (1987) 97–126. One of the vibration tests discussed therein used a container enclosing a granular charcoal bed which was vibrated at 60 Hz with an acceleration of 5 g. Air was blown into the top of the container and dust formed by the attrition of the granular charcoal passed through the perforated base of the container to be collected on a glass fiber filter paper. As a result, the impact strength of the entire bed was tested and not individual particles.

Another vibration test is reported in T. P. Ponomareva, S. I Kontorovich, and E. D. Shchukin, Attrition Of Spherical Cracking Catalysts in the Presence Of Powdered Lubricants, *Kinetics and Catalysis*, 21 (1980) 505–510 for measuring the wear between catalyst particles treated with a lubricant powder. The test used a specially constructed cylindrical drum undergoing vertical vibrational movement imposed by a vibro-saw at a frequency of 50 Hz and an amplitude of 6 mm. Only the amount of wear between the catalyst particles themselves could be measured by removing the abrasion products through sieves located in the drum.

These methods have proven unsuitable for characterizing the individual particle since these methods vibrate an entire bed within a closed vessel. They measure the particle to vessel-wall interaction when the attrition and fragmentation of the particles is primarily caused by the particles rubbing each other. The impact velocity of the collisions encountered by the particle bed is also poorly defined by these methods and may be inaccurate due to some collisions encountering drag forces within the bed. Furthermore, some of these methods only measure spherical particles and are poorly adapted to accurately characterize aspherical or non-uniform shaped particles.

Thus, a need exists for a method and device for assessing attrition and fragmentation characteristics of particles during handling. A tool is needed to help develop particles which are individually strong since the mechanically stability of the particle is of primary importance in many industrial fields such as enzyme formulation technology. Characterizing the impact strength of individual particles, as opposed to entire particle bed, provides information that can be used to develop particles with enhanced attrition strength.

SUMMARY OF THE INVENTION

The present invention provides a test device for characterizing the impact strength of a granule. The test device includes a first container having an interior cavity larger than the size of the granule and means for vibrating the first container in a generally unidirectional movement at a predetermined frequency of resonance with sufficient strength to provide reproducible damage to the granule, the vibrating means connected to the first container.

The present invention also provides a test device for characterizing the impact strength of a granule which includes a vibrator providing a generally unidirectional movement at a predetermined frequency and a first container having an interior cavity larger than the size of the granule. The device further includes a first spring configured to connect at one end to the vibrator. The opposite end of the first spring is configured to connect to the container. The first spring has a predetermined frequency of resonance adapted to amplify the frequency of the vibrator movement and impart the amplification to the container.

A method of characterizing the impact strength of a granule is also provided by the present invention. The method includes the steps of: vibrating a sealed container having an interior space for confining a plurality of granules at a predetermined resonant frequency for a predetermined period of time and amplitude to cause repeated impact of the granules against the interior walls of the container; removing dust, fines and damaged granule fragments that do not exhibit a minimum desired size, from the container; and measuring the amount of undamaged granules and only slightly damaged granules that do exhibit the minimum desired size.

A method for characterizing the attrition rate of a granule is also provided by the present invention. The method includes the steps of: disposing granules to be tested within a closed container; repeatedly impacting the granules within the closed container such that granule damage occurs; removing dust, fines, and small granules and small granule fragments that do not exhibit a first minimum desired size; measuring the weight of undamaged granules and large damaged granules that exhibit the minimum desired size, as a consequence of a number of collisions between the granules and the container walls; again repeatedly impacting the undamaged granules and large damaged granules within the closed container such that granule damage occurs; removing dust, fines, and small granules and small granule fragments that do not exhibit a second minimum desired size; again measuring the weight of the undamaged granules and damaged granules that exhibit the second minimum desired size, as a consequence of a number of collisions with the container walls; and determining the attrition rate of the granules measured as the weight of dust generated per number of collisions or as a function of the weight of the granules relative to the original weight of the granules. Removing the dust, fines, small granules and small granule fragments that do not exhibit the desired minimum size can preferably be accomplished by sieving the impacted granules to separate the larger damaged and undamaged granules from the smaller dust, fines, fragments, and damaged granules.

Accordingly, it is an object of the present invention to provide a method and device for characterizing the impact strength of an individual granule.

Another object of the present invention is to provide a method and device which is adaptable to characterizing aspherical or non-uniformly shaped granules and accurately relates single granule to multiple granule results.

It is a further object of the present invention to provide a device which provides a higher number of well-controlled impacts for each granule compared to the prior art.

Still another object of the present invention is to provide a test device which is inexpensive to build and operate for a large number of representative samples to yield reproducible test results easily obtained without extensive operator training.

A further object of the present invention is to provide a test device which provides granules with collision orientations which are equally likely and minimizes drag force.

Other and further advantages, embodiments, variations and the like will be apparent to those skilled-in-the-art from the present specification taken with the accompanying figures and appended claims. The accompanying figures, which are incorporated in and constitute a part of this application, illustrate several exemplary embodiments of the present invention and together with description, serve to explain the principles of the present invention.

BRIEF DESCRIPTION OF THE DRAWINGS

The invention may be more fully understood with reference to the accompanying figures which are intended to illustrate the invention without limiting the scope of the invention.

DESCRIPTION OF THE PREFERRED EMBODIMENTS

Figure 1:
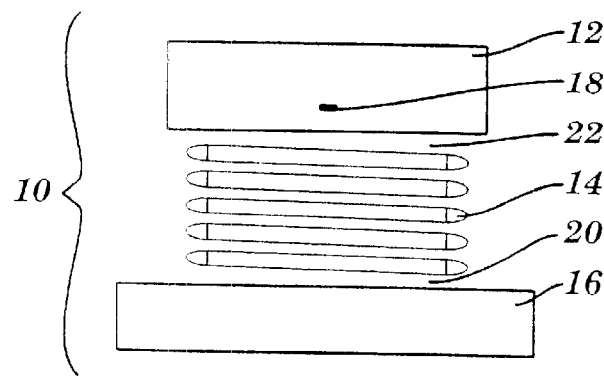
FIG. 1 is a side view of a schematic illustrating a test device for measuring the impact strength of a granule as provided by the present invention.

The present invention provides a method and device for measuring granule impact strength by vibrating a small container of one or more granules at a well-controlled amplitude in order to inflict reproducible damage to the granules. Damage to the granules is measured as a function of time and amplitude. The measurements obtained yield a highly reproducible means for characterizing granule attrition and fragmentation.

The term attrition as used herein includes the unwanted breakdown of particles within a process. Attrition includes both abrasion and fragmentation provided these are unwanted. Fragmentation is the process whereby a particle splits into smaller parts, usually large in number and including a range of sizes of particles produced by the breakage of larger particles. Abrasion is the removal of material from a particle such that the material removed is much smaller than the particle.

The term granule as used herein includes one or more particles or an agglomerate. An agglomerate is an assemblage of particles which are either loosely or rigidly joined together. A particle includes a piece of material which is an entity in itself. It may be porous or contain faults or cracks, but in general has not been formed by joining together two or more smaller pieces of material.

Damage to granules can be inflicted by creating a defined strain upon the granules through a number of different methods. For example, the direction of the strain of a compressive force with respect to the geometry of the granules can be changed. The geometry of the force can vary to exert either an impact, slow compressive, or very fast compressive force. The strain can be dependent on the shape and size of the granules.

As discussed above, one of the problems with using the current methods is receiving reproducible, and thus more useable, results. When inflicting damage towards a granule, it is difficult to inflict the damage in a reproducible way. Without a reproducible starting point, the results are spread over a wide range and are difficult to interpret. If this problem is overcome by reproducibly inflicting damage, the spread in the results are reduced significantly. The test results presented herein using the present invention will demonstrate a more reproducible method of inflicting damage and more meaningful results compared to the current methods.

Another problem with using these methods previously discussed is that only granules with well-controlled fabrication histories are well-suited for measurement. When a granule is deformed, inhomogeneities can concentrate local stresses and can seriously reduce granule strength. In general, the granule will be inhomogeneous, asymmetrical and aspherical. When a granule has been built up using layering techniques, the inhomogeneities which are accidental will be observed. The presence of cracks in the granules can be important for determining granule strength. The fabrication history of the granule such as the number of impacts, observed temperature or humidity gradients can affect the determination of granule strength. The present invention is not so limited and provides a reproducible measurement of the strength of the individual granule even though it is affected by the geometry of the strain, the velocity of the impact or strain, the direction of the force and the size and shape of the granules.

The present invention provides a test device 10 having a container 12 mounted on a spring 14 which, in turn, is mounted on a vibrator 16. The container 12 is preferably made of a light weight metal, such as aluminum, which is strong and seals dust-tight. The container preferably has very rigid, stable and robust inner wall surfaces that provide a coefficient of restitution that equals or approximates one, and preferably that does not change over time. A granule 18 is confined within the container 12 for testing. The height of the container 12 is much larger than the diameter of the granule 18 (preferably, in excess of about 50 times). Having the dimension of the container 12 in the direction of the container's travel so much larger, provides the granule 18 with free movement within the container for a longer period of time. High impact velocities result when the container 12 has more time to decelerate before impacting the granule 18 and creates a larger velocity difference between the wall of the container and the granule.

The container 12 preferably vibrates with an amplitude that is at least about one-half, and preferably larger than, the height of the container 12 to assure that the granule 18 inside the container 12 is forced to bounce off both the top and bottom walls of the container 12. The amplitude of the vibration is proportional to the velocity of the container 12. Preferably, the granules are shaken with accelerations up to about 400 g at amplitudes from about 0.25 cm to about 4.0 cm.

The spring 14 is selected accordingly to have a predetermined frequency of resonance such as, for example and not limited to, about 50 Hz. The vibrator 16 shakes with a small amplitude at the selected resonance frequency which results in strongly amplifying the movement imparted to the container 12. For example, when the vibrator 16 shakes with an amplitude of only about 1 mm at one end 20 of the spring 14, the container 12 can easily reach amplitudes of about 50 mm at the other end 22 of the spring. Any conventional vibrator, preferably having a vertical motion, is suitable for use with the present invention. One example is a vibrating table.

The test device 10 provides a means to make the granules collide with the walls of the container 12 in a well-controlled manner. By adjusting the mass of the container 12 (adding or subtracting small amounts of mass), the total mass spring system can be fine tuned to yield a resonance frequency. Preferably, the resonance frequency of 50 Hz (European mains) is used.

In operation, the container 12 is subjected to several predetermined periods of vibration. The percentage of mass of undamaged granules is determined after each period of vibration. The damaged granules are removed from the container 12 by passing them through an appropriately sized sieve. Preferably, a sieve having a size of about 40 mesh is used, although any of a variety of mesh sizes can be used, depending upon, for example, the starting size of the granules to be tested, the coating layer thickness of the granules to be tested, the number of collisions, and the desired granule size to be separated. For instance, if the starting average diameter of the granules to be tested is about 600 microns, the sieve used to separate large damaged granules and large undamaged granules from dust, fines, small granule fragments, and small granules, may preferably have openings of about 425 microns. Sieves having openings of from about 60% to about 80% of the average granule diameter of the starting granules, are preferred for separating granules to be measured after a first round of impact testing. Progressively smaller sieve opening sizes can be used for subsequent impact testing of the remaining measured granules.

Determining the number of undamaged granules and/or damaged granules of a desired minimum size, still present after impact testing yields the percentage of granules not fragmented. With this information, the development from attrition to fragmentation can be monitored.

Figure 2:
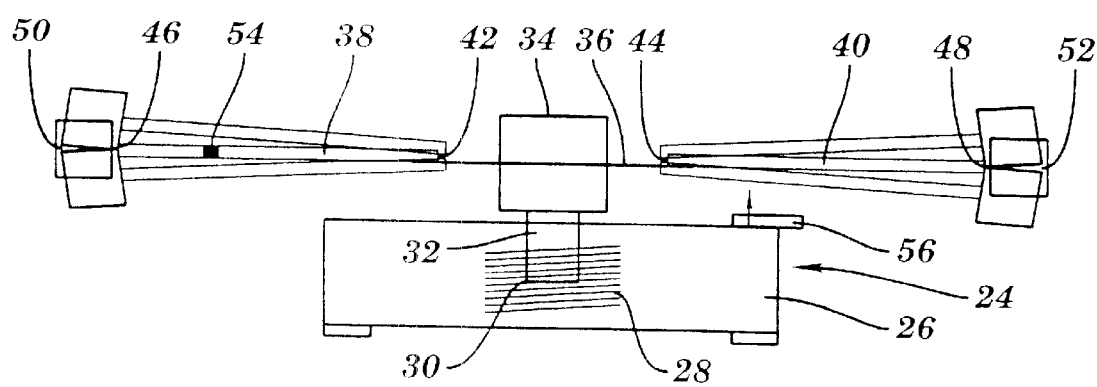
FIG. 2 is a side view of a preferred embodiment of a test device provided by the present invention with a portion of the device box cut-away to illustrate the internal spring mechanism.

A preferred embodiment of the inventive test device for dynamically testing the strength of a granule is illustrated in FIG. 2. The test device 24 includes a housing 26 for supporting a spring 28 therein. The spring 28 connects to one end 30 of a rod 32 extending externally from the housing 26. Connected to the opposite end 34 of the rod 32 is an elongated support which connects to a tempered blade spring 36. A pair of rigid arms 38, 40 connect at one end 42, 44 to opposite sides of the blade spring 36. The other ends 46, 48 of the rigid arms 38, 40 connect to a pair of containers 50, 52, respectively. Preferably, the arms 38, 40 are made of aluminum and are attached in a symmetrical arrangement centered on the blade spring 36 in order to avoid problems with impulse-momentum stability. A small weight 54 slidably attached along the longitudinal direction of one, or both, arms 38, 40 can be used to adjust the resonance frequency of the containers 50, 52.

Figure 3:
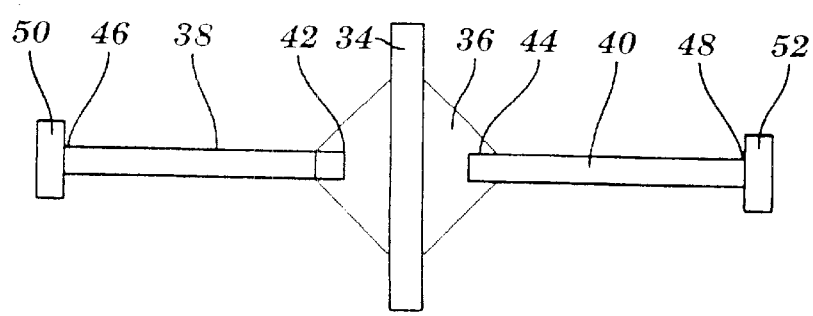
FIG. 3 is a top surface view of the device in FIG. 2 isolating the symmetrical blade spring, containers and vibrator.

FIG. 3 illustrates in greater detail the blade spring 36 rigidly connected to the end 34 of the rod along the elongated support. Since conventional wound springs are too heavy for reaching high resonance frequencies, the present invention adds a second spring means by utilizing the blade spring 36. The shape and material comprising the blade spring 36 allows flexing to occur between the ends 42, 44 of the rigid arms 38, 40 and the end of the rod 34. The flexing of the blade spring 36 allows the containers 50, 52 to reach a higher resonance frequency.

The amplitude achieved by the containers 50, 52 based on the concept of the resonating spring blade 36 is illustrated by the phantom images in FIG. 2. As the agitation is near to the resonance frequency of the mass spring combination, large amplitudes can be achieved. The frequency of operation is dictated by the mains which is preferably about 50 Hz. Therefore, the container travels a complete cycle about every 20 milliseconds (ms).

In operation, both containers 50 and 52 can be used for testing granules. It has been observed, however, that when the amplitude of one container of the test device 24 is declined, additional energy appears to be directed to the other container, yielding a higher amplitude. This provides the opportunity for a robust mechanical feedback for amplitude regulation when only one container of the test device 24 is used for granule testing. The amplitude of the container with the granule is simply restricted to a certain maximum. Enough energy is applied to the test device 24 so as to ensure a regulating effect of the mechanical feedback. All excess energy is then directed by the test device 24 to the container which is not being used to test the granule.

The amplitude can be controlled easily by installing a mechanical limit 56 to the allowed travel of the resonating system. An amplitude is set in the vibration test by adjusting the height of the mechanical limit 56.

Another preferred embodiment is useful when hardly any damage is found using the test devices described above. In this alternate embodiment, one or more metal balls are added to the container with the granules. For example, in measuring catalyst particles of 70 μm size, a single metal ball of 4 mg is added to the container. Any object having an impact strength significantly larger than the granule and a diameter less than the interior cavity of the container is suitable for use in the present invention. Damage is observed by sieving over 50 μm.

Due to the oscillating behavior of the container, the metal ball situated inside the container is forced into synchronized motion, bouncing from side to side every 20 ms. Damage occurs to granules also present in the container from collisions between the metal ball and the granules or from collisions between the granules and the container walls. With every cycle of the container several collisions are possible, although collisions cannot be guaranteed.

This mode of operation for the present invention differs from the collisions previously described directly between the granules and the walls of the container. It is guaranteed that in every cycle of the container, each granule collides with the container wall and in this way many random orientated collisions are obtained, all with a very defined impact velocity. As a result, all possible collision orientations will occur within a short time period.

Figure 6:
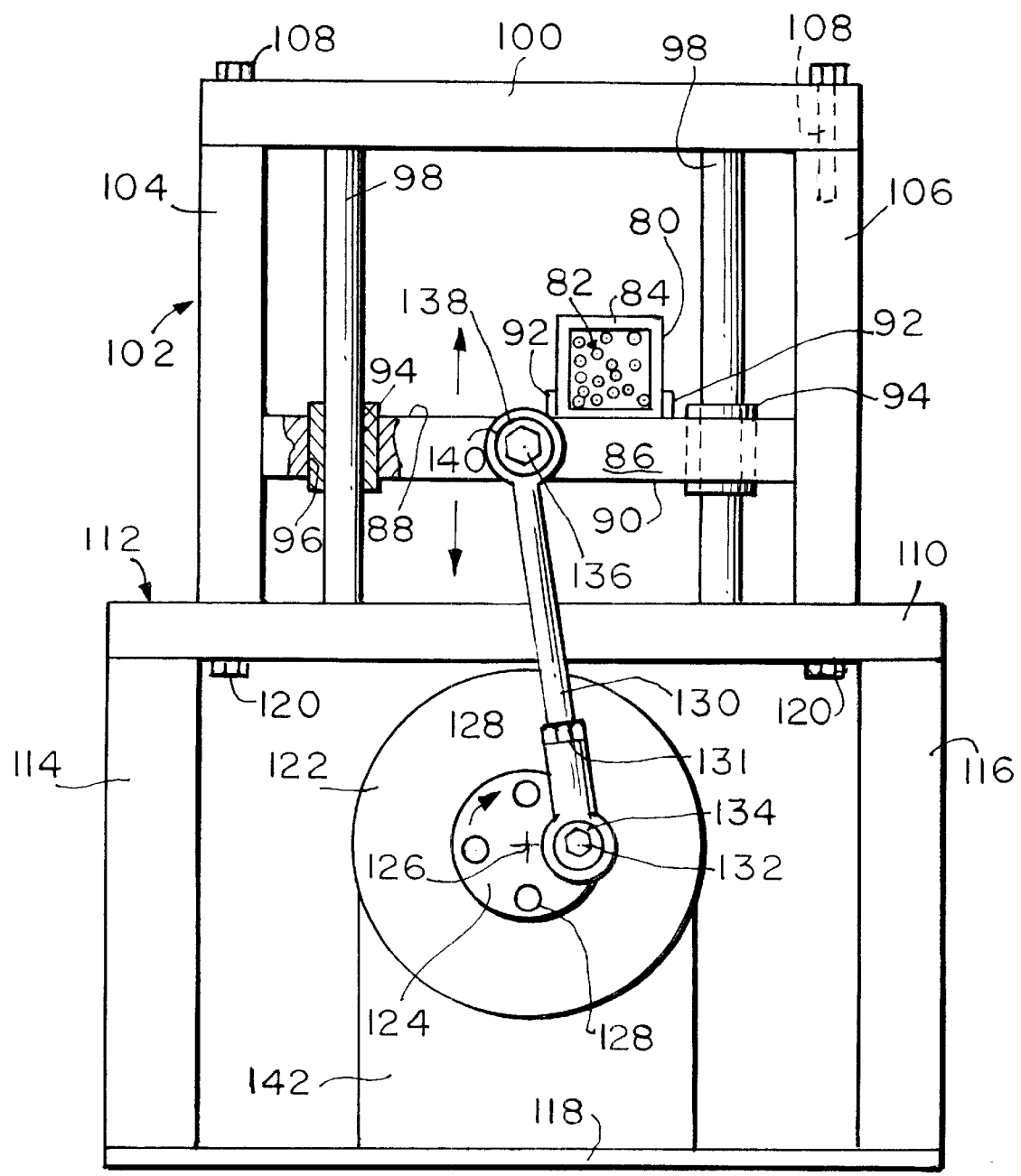
FIG. 6 is a front plan view in partial cutaway of a reciprocating repeated impact testing machine according to an embodiment of the present invention.

Referring now to FIG. 6, a repeated impact testing device according to yet another embodiment of the present invention is shown. According to the embodiment of FIG. 6, a crank and slider type device is provided which can exert a unidirectional movement of a container that contains a sample of granular material, for example, coated enzyme granules. The design of the device shown in FIG. 6 provides repeated impact of granules contained in the container in a unidirectional movement and substantially only against the inner surfaces of a top wall and bottom wall of the container, with little or no tangential velocity component and thus little or no impact forces of the granules against the side walls of the container. The device is very robust and in the embodiment of FIG. 6 no springs are required.

According to the embodiment of FIG. 6, a container 80 is provided and contains therein a singular granule, or, as shown, a plurality of granules 82 to be tested. The container shown has four side walls although other shapes including other numbers of sidewalls, such as a cylindrically-shaped container having a single side wall, can be used in accordance with the present invention. The container preferably has a removable and reclosable top 84 that can be removed or replaced as needed to position a sample of granules in the container or to remove a sample tested from the container. The container 80 can be secured or mounted by any of various means to a reciprocated platform 86 having a top surface 88 and a bottom surface 90. Fixed to the top surface 88 of the platform 86 are mounting brackets 92, in the embodiment shown, used to fix the container 80 onto the top surface 88. Any conventional securing means, such as hook and loop fasteners, magnetic fasteners, or other fasteners can alternatively be used in place of or in addition to the mounting brackets.

The platform 86 is provided with bushings, bearings, or preferably ball bushings 94 fixed or secured in holes 96 formed in the platform 86. The bushings 94 may comprise a polished metal material or a low friction hard plastic material such as polytetrafluoroethylene. The bushings may be housed in respective ball bushing bearing blocks mounted on an edge of the platform 86. The bushings facilitate a smooth reciprocating motion of the platform 86 up and down along two guide rods, shafts or sliders 98 as shown. Preferably, the guide rods 98 comprise a smooth, hardened metal material, for example, polished steel.

Preferably, at least two guide rod and ball bushing sets are provided to ensure a smooth unidirectional movement of platform 86. For example, four or eight sets of guide rods and ball bushings can be provided on, in, through, or attached to the platform 86 to guide the movement of the platform in a unidirectional travel direction.

The top ends of each guide rod 98 are secured, fixed, or otherwise mounted to a top plate 100 of a guide rod support assembly 102. Guide rod support assembly 102 also includes vertical side wall members 104 and 106 that are respectively connected at upper ends thereof to top plate 100, for example, by bolts 108. The vertical side walls 104 and 106 are connected at the bottom ends thereof to a top plate 110 of a support assembly 112. The support assembly 112 also includes vertical side walls 114 and 116 and a bottom plate 118. The vertical side walls 114 and 116 of the support assembly 112 are likewise connected to the bottom plate 118 by bolts or other connection means. The guide rod support assembly 102 and the support assembly 112 preferably comprise metal components, such as aluminum side walls, top plates and an aluminum bottom plate.

The platform 86 can be of any shape and is preferably rectangular in shape as shown. The platform 86 is reciprocated in an up and down unidirectional movement by the camming or piston action of a connection arrangement to a motor 122. In the embodiment of FIG. 6, the motor 122 powers a rotating axle (not shown) having connected to an end thereof a drive wheel 124. The drive wheel 124 rotates about an axis of rotation 126. Offset from the axis of rotation 126 of the drive wheel 124 are threaded mounting holes 128. A piston rod 130 is connected to the drive wheel 124 via a bolt 132 that passes through a hole in the end of piston rod 130 and threadably engages one of the threaded mounting holes 128. A washer or bushing 134 is provided so that piston rod 130 can move freely about the shaft of bolt 132 when bolt 132 is secured in one of the threaded mounting holes 128. Upon rotation of the drive wheel 124, for example, in the direction shown by the arrow drawn on drive wheel 124, piston rod 130 is alternately pulled downward and pushed upward to cause reciprocating motion of platform 86. The upper end of piston rod 130 is connected to platform 186 via a bolt 136 and washer 138 to allow movement of the top end 140 of piston rod 130 while bolt 136 is securely fastened to platform 86. A mount 142 is provided to secure motor 122 to the bottom plate 118 of the support assembly 112.

The amplitude of the up and down reciprocating motion of platform 86 and container 80 can be varied by switching the threaded mounting hole 128 with which bolt 132 is engaged. The hole 128 closest to the axis of rotation 126 of drive wheel 124 provides the smallest amplitude of movement of platform 86 whereas the hole 128 farthest from the axis of rotation 126, that is, the hole engaged by bolt 132 as shown in FIG. 6, provides the greatest amplitude. Piston rod 130 can be telescopic as shown and the length of piston rod 130 can be adjusted by turning adjustment nut 131.

The motor 122 can be any suitable drive source including an induction motor, an electric motor, a pneumatic pump, or an internal combustion engine. Preferably, motor 122 is an electric motor including an inverter drive that provides a variable speed output to turn drive wheel 124. Suitable controls (not shown) or gears (not shown) can be provided to control the speed of rotation of drive wheel 124.

Other advantages of the embodiment of FIG. 6 include the ability to control effectively the frequency of oscillation of the platform by changing the rotational speed of the drive wheel. Also, because the velocity of impact of the particles is dependent on the frequency of oscillation as well as the stroke of the platform, the speeds can be varied with two operating parameters. A higher impact velocity can be achieved by either increasing the frequency or stroke, or both. Increasing frequency not only increases the velocity but also reduces the time of the test. In addition, the platform can handle larger sample sizes as the power of the motor connected to the drive wheel can be very high. A large sample in a large product container reduces the probability of inter-particle collisions and at the same time produces statistically correct results useful for a standard test.

Figure 7:
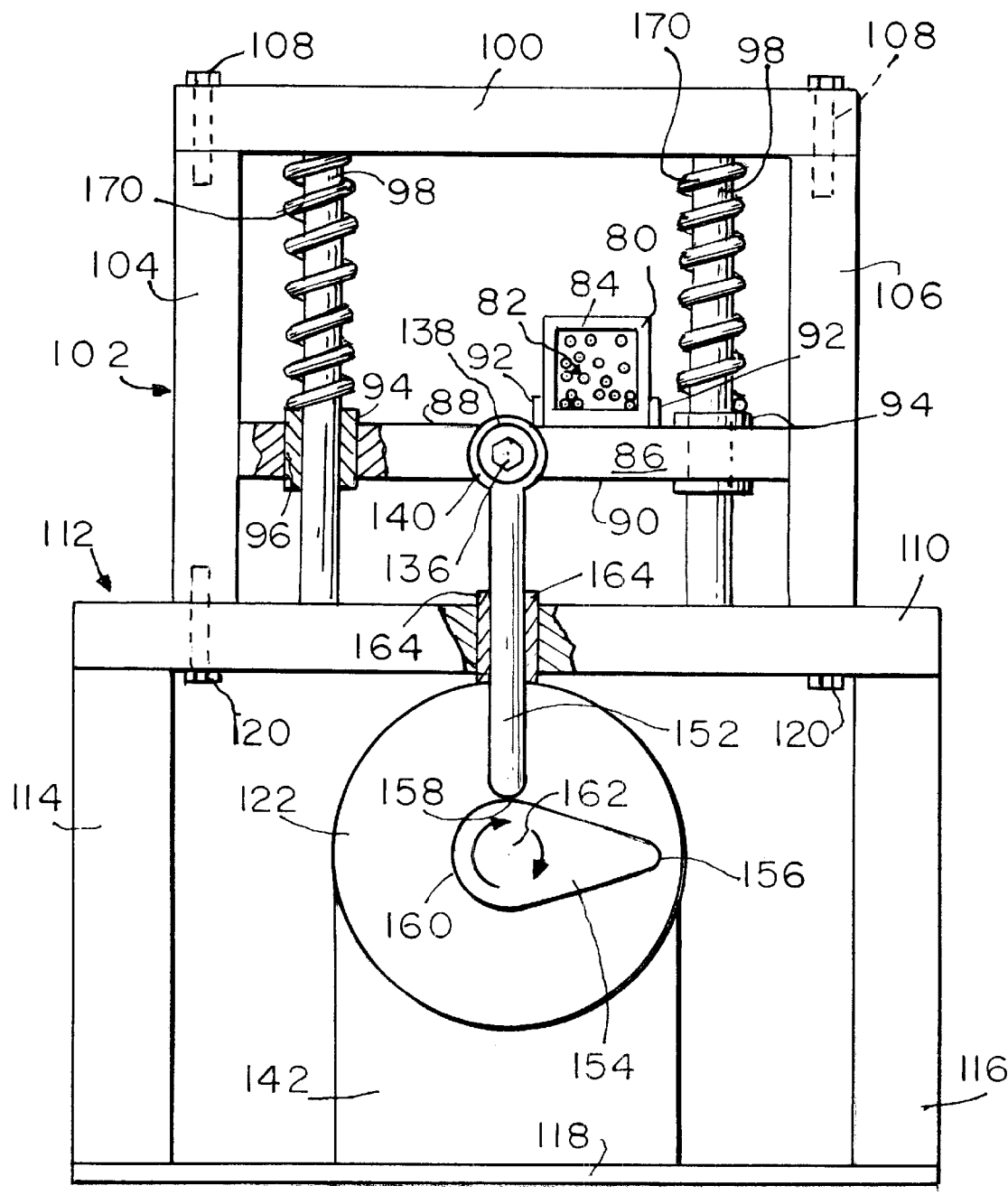
FIG. 7 is a front plan view in partial cutaway of a reciprocating repeated impact testing machine according to another embodiment of the present invention.

Another embodiment of the present invention is depicted in FIG. 7 wherein like reference numerals represent like components relative to FIG. 6. As shown in FIG. 7, the platform 86 is reciprocated by the up and down motion of a push rod 152 that rides on a cam 154 rotated by a drive axle of motor 122. As the cam 154 rotates in the direction shown by the two arrows on the cam, push rod 152 rides along the surface of cam 154 and reaches a highest point when pinnacle 156 of cam 154 contacts the bottom end 158 of push rod 152. As the cam 154 rotates the platform 86 reaches its lowest point as the end 158 of push rod 152 contacts low point 160, which is opposite pinnacle 156 with respect to the axis of rotation 162 of cam 154. The end 158 of push rod 152 can be biased against the surface of cam 154 due to the weight of platform 86. Other biasing means, such as springs 170 as shown can be used to bias the end 158 of push rod 152 against the surface of cam 154.

As shown in FIG. 7, push rod 152 is guided to assure unidirectional travel by passing through a bushing 164 fixed, secured, or otherwise mounted within a hole in the top plate 110 of support assembly 112. In the embodiment shown in FIG. 7, bushing 164 and top plate 110 are shown in partial cutaway. As shown, bushing 164 is mounted in a hole through top plate 110 but the bushing could instead by secured to a front side edge of top plank 110. Pushrod 152 fits snuggly within bushing 164 such that horizontal movement or vibration of pushrod 152 is minimized or preferably completely avoided and movement of pushrod 152 and thus platform 86 is limited to unidirectional vertical movement.

According to yet another embodiment of the present invention, a method of characterizing granule strength is provided wherein the granules, particularly multilayered granules, are subjected to a repeated impact test and the attrition rate of the granules is plotted as a function of either the mass of the granules, the change of mass of the granules, or both. For some granules, particularly multilayered granules, it is important to characterize the attrition rate of the granule as the outer surface, an outer layer, or an outer coating of the granule is worn. It has been discovered according to the present invention that the attrition rate of a granule during breakage testing and normal wear conditions can vary greatly very depending upon the composition of the outermost surface of the granule. For example, for a multi-layered granule having a polymeric overcoat, it has been found that the attrition rate of the granule is large at the beginning of a repeated impact test. As the polymeric overcoat becomes slightly worn or broken down, it has been found according to the present invention that the attrition rate of the granule decreases until an interface between the polymeric overcoat and the core of the granule is reached. It has also been discovered according to the present invention that once the polymeric overcoat of the granule is worn or broken down from repeated impact testing, the attrition rate of the granule greatly increases at about the interface between the core of the granule and the polymeric overcoating. After the polymeric overcoat has been worn away from the granule, it has also been found that the attrition rate of the granule dramatically decreases once the core alone remains.

According to embodiments of the present invention, the attrition rate (A) of a multilayered granule tested in accordance with a repeated impact test method and device of the present invention can be calculated from the following equation:

$$A = \Delta M / \Delta n = (M_f - M_i)/(n_f - n_i)$$

wherein M is the mass of the granules during the test and n is the number of collisions that have taken place. Subscripts "i" and "f" refer to initial and final, respectively, as in the initial and final mass and the initial and final number of collisions. An example of such a calculation is shown below in Example 5.

Having generally described the present invention, a further understanding can be obtained by reference to the following specific examples, which are provided herein for purposes of illustration only and are not intended to be limiting of the present invention.

EXAMPLE 1

Figure 4:
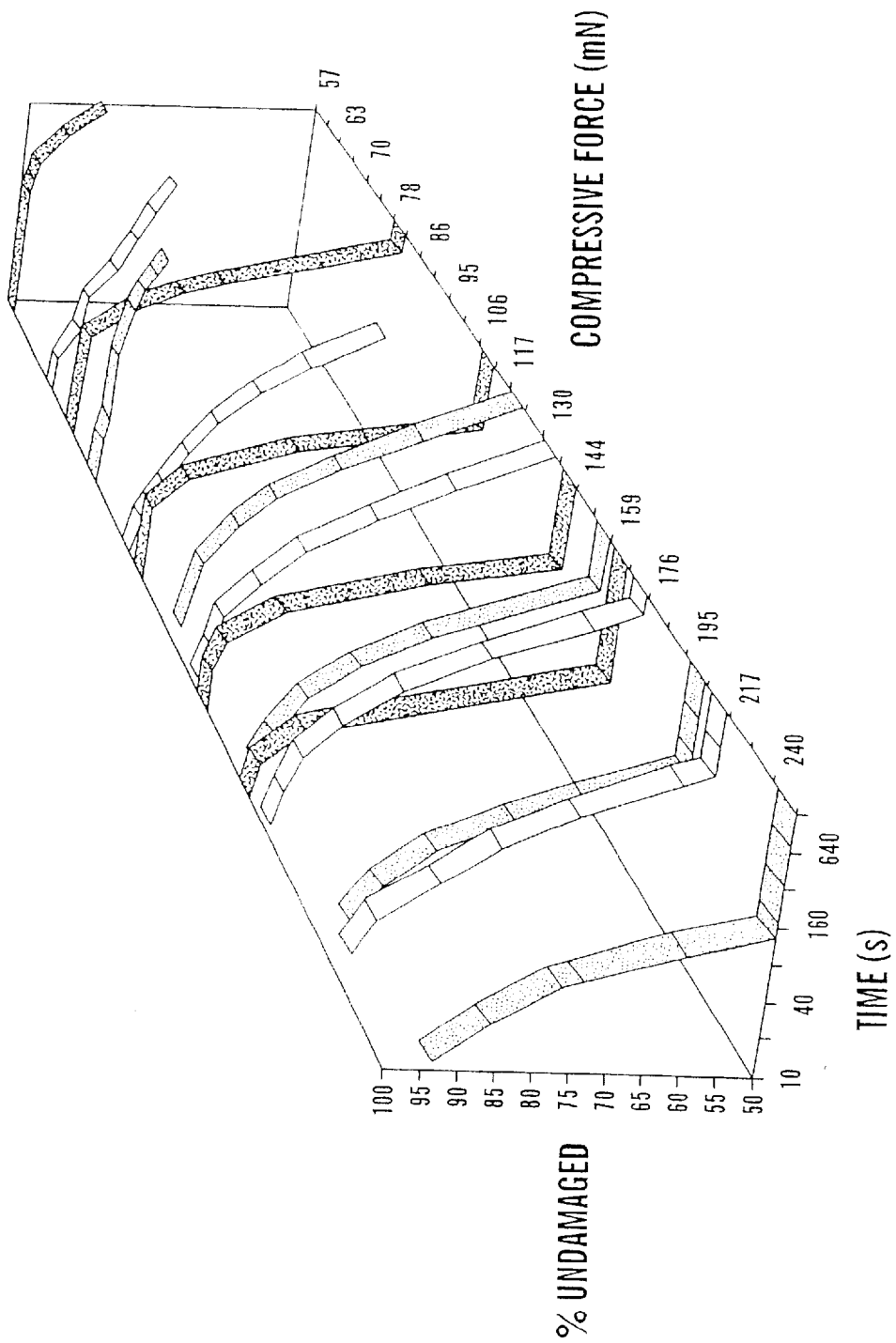
FIG. 4 is a graph of the percentage of undamaged particles versus time across a range of different compressive forces.

Unless otherwise stated, the following procedure was used in obtaining the test results presented in the tables and FIG. 4. Using the preferred embodiment test device 24, the amplitude was set in the vibration test by adjusting the height of the mechanical limit. The containers were made of plastic having a height of about 2.5 cm and were thoroughly cleaned.

The preferred length of each rigid arm 38, 40 and container 50, 52 was about 15 cm. The amplitude of vibration was controlled in the preferred range of about 0.5 cm to about 2.0 cm.

About 30 mg of granules (which is about 150 pieces) having a size range of about 0.4 mm to about 1.0 mm were put into one of the plastic containers. The container was sealed dust tight with adhesive tape. The container was shaken during an interval of time into its resonance frequency (for example 10 s, 20 s, 40 s and 80 s). After each period of time, the contents of the container were sieved using a 315 μm sieve to remove the damaged granules.

By taking pictures of the undamaged fraction, it was possible to determine the proportion of attrition versus fragmentation. The percentage of mass that was unbroken was determined and this fraction was put back into the container. The container was sealed and shaken for another interval of time.

This was repeated for a number (n=5) of different amplitudes by adjusting the mechanical limit. A three dimensional picture was formed by plotting either attrition or breakage as a function of velocity and the number of repetitions.

The test device was first used to demonstrate that the results were not influenced by the number of granules tested at one time. Table 1 reports the results from using enzymes containing layered granules.

TABLE 1

| Layered Granules | | | |
|---|---|---|---|
| Time (s) m = mass n = number [mg] of granules | | | n = number of granules |
| | m retained | n = 10 [%] | n = 309 [%] |
| 0 | 1.36 | 100 | |
| 20 | 1.07 | 79 | |
| 60 | 0.86 | 63 | |
| 80 | 0.68 | 50 | |
| 160 | 0.23 | 17 | |
| 320 | 0.21 | 15 | |
| 0 | 41.99 | | 100 |
| 10 | 41.44 | | 99 |
| 20 | 39.87 | | 95 |
| 40 | 34.14 | | 81 |
| 80 | 23.68 | | 56 |
| 160 | 11.22 | | 27 |
| 320 | 6.14 | | 15 |

One of the advantages of running tests on a larger number of granules is to reduce the difference between samples and the inaccuracy of determining the granules' weight. Furthermore, fragmentation is a discrete effect, so large numbers of granules are required for obtaining smooth, more meaningful signals. A suitable method of damage assessment for larger samples is to sieve over half the original granule size e.g. 310 $\mu$m when granules of about 600 $\mu$m are used It appears that smaller sieves can be used as well, as granule fragments are quickly reduced to a small size.

EXAMPLE 2

A series of tests was carried out with three commercial available granules: Genencor CXT 600.00 prills (prills), Genencor Fluid Bed Granules (FBG) from Genencor and Savinase 4.0T from NOVO Nordisk (Enzyme Layered Granules-(ELG)). Results are listed in Tables 2, 3, and 4. It was that the results appear independent from the amount of granules in the test within the range identified in the above Example. The spread in the results appears to be very low (on average less than 2% for 25% of damage).

About 30 mg of each commercially available granule product was introduced into the test and vibrated with different amplitudes of the container for several time intervals. After each period the amount of undamaged granules was determined by sieving the granules over 315 $\mu$m.

Table 2 gives the results for granule product ELG. Observing the results across the columns, the effect of increasing the amplitude [A] of the container can be monitored. Average particle size in the tests was between 590 and 710 $\mu$m, average granule mass was determined from counting the number of granules introduced to the test: 0.29 mg.

TABLE 2

| ELG | ELG Undamaged [m %] A[cm] | | | | |
|---|---|---|---|---|---|
| time[s] | 2 | 1.7 | 1.3 | 1 | 0.7 |
| 10 | 93 | 95 | 97 | 98 | 100 |
| 20 | 86 | 91 | 95 | 97 | 100 |
| 40 | 77 | 84 | 91 | 96 | 99 |
| 80 | 61 | 73 | 84 | 92 | 99 |
| 160 | 41 | 58 | 74 | 86 | 99 |
| 320 | 21 | 39 | 58 | 77 | 98 |
| 640 | 7 | 17 | 40 | 65 | 96 |
| 1280 | 3 | 7 | 24 | 51 | 93 |

EXAMPLE 3

Table 3 gives the results for granule product Prill. Again, about 30 mg of product was introduced into the test and vibrated with different amplitudes for several time intervals. After each period the amount of undamaged granules was determined by sieving over 315 um. The average granule size was between 590 and 710 um, average granule mass was determined from counting the number of granules introduced to the test: 0.17 mg.

TABLE 3

| Prill | Prill undamaged [m %] A[cm] | | | | |
|---|---|---|---|---|---|
| times[s] | 2 | 1.7 | 1.3 | 1 | 0.7 |
| 10 | 97 | 99 | 99 | 100 | 100 |
| 20 | 94 | 98 | 98 | 99 | 100 |
| 40 | 86 | 96 | 97 | 96 | 97 |
| 80 | 78 | 91 | 92 | 93 | 96 |
| 160 | 68 | 83 | 86 | 89 | 92 |
| 320 | 54 | 71 | 76 | 83 | 89 |
| 640 | 38 | 57 | 65 | 76 | 87 |
| 1280 | 15 | 40 | 51 | 65 | 84 |

EXAMPLE 4

Table 4 gives the results for the granule product FBG. About 30 mg of product was introduced into the test and vibrated with different amplitudes for several time intervals. After each period, the amount of undamaged granules was determined by sieving over 310 um. Average particle size in the experiments was between 590 and 710 um, average particle mass was determined from counting the number of granules introduced to the test: 0.16 mg.

TABLE 4

| FBG | FBG Undamaged [m %] A[cm] | | | | |
|---|---|---|---|---|---|
| time[s] | 2 | 1.7 | 1.3 | 1 | 0.7 |
| 10 | 100 | 100 | 100 | 100 | 100 |
| 20 | 99 | 100 | 100 | 100 | 100 |
| 40 | 92 | 99 | 100 | 100 | 100 |
| 80 | 68 | 91 | 95 | 100 | 100 |
| 160 | 40 | 70 | 79 | 94 | 100 |
| 320 | 22 | 37 | 51 | 80 | 99 |
| 640 | 11 | 16 | 26 | 58 | 95 |
| 1280 | 5 | 9 | 15 | 40 | 88 |

The results measured by the present invention and reported in Tables 2, 3, and 4 provide information not easily made available by the current methods. The results across the rows of the Tables identify the cumulative strength distribution of the granules as a function of their fatigue history. The results across the columns of the Tables identify the development of the percentage undamaged as a function of fatigue.

One interpretation provided by each of the Tables is a comprehensive description of the strength behavior of the granule during dynamic processes such as pneumatic transport and dosing. During pneumatic transport, granules suffer from collisions with the wall in a comparable way as the collisions generated in the tests of the present invention. Thus, the tests provide an indication of the damage occurring to the granules during transport.

Using constant velocities as the criterion, tests at constant amplitude should be compared.

Another interpretation provided by each of the Tables is the fatigue caused by dynamic and static compressive forces. Since amplitude is easily varied and the number of collisions is controlled by the duration of each test, a complete characterization is available for granule fatigue as a function of velocity of impact. As for low velocity impacts (about 10 m/s) most deformation of the granules is primarily elastic. One can convert velocity of impact to compressive force of impact when the compressibility constant is known.

With this information, different types of granules can be compared by their fatigue results. Effects of differing mass can be incorporated if, as a first approximation, elastic collisions are assumed: $0.5 \ mv^2 = 0.5 \ F_{max}^2/S$, where S is granule stiffness and the maximum occurred compressive force. Thus, $F_{max} = v\sqrt{(mS)}$. Granule stiffness as used herein is the initial linear relation between granule deformation and required compressive force. Table 5 presents the mean result of measurements of granule stiffness for the three commercial granule products tested herein which allows calculation of the compressive forces in the impact tests.

TABLE 5

|  | Stiffness [N/mm] |
| --- | --- |
| ELG | 10.6 |
| Prill | 14.6 |
| FBG | 13 |

Using the formula for $F_{max}$, the maximum compression force during impact can be calculated and the influence of mass of granules during impact can be incorporated. The calculated forces using container velocities, average mass and granule stiffness, for each commercial granule product tested herein is presented in Table 6.

TABLE 6

| A[cm] | ELG v[m/s] | F[N] | FBG v[m/s] | F[N] | Prill v[m/s] | F[N] |
| --- | --- | --- | --- | --- | --- | --- |
| 2.0 | 3.9 | 0.24 | 3.9 | 0.16 | 3.9 | 0.19 |
| 1.7 | 3.2 | 0.2 | 3.2 | 0.14 | 3.2 | 0.17 |
| 1.3 | 2.6 | 0.16 | 2.6 | 0.1 | 2.6 | 0.13 |
| 1.0 | 2.0 | 0.12 | 2.0 | 0.08 | 2.0 | 0.10 |
| 0.7 | 1.3 | 0.08 | 1.3 | 0.06 | 1.3 | 0.07 |

The tests performed by the present invention are extremely well-defined in terms of impact velocity, impact orientation, impact force and history of the granules. Therefore, it is an extremely well-defined test for granule fatigue. Plotting the results as a function of fatigue presents a very clear picture of particle strength which can not be readily obtained using the prior art methods.

In FIG. 4, the results for the three different types of granule products are given as a function of fatigue parameters (force of fatigue and duration). The fatigue force has been calculated as described earlier. Clearly, results for a single type of granule are strongly related and appear to create three dimensional curved surfaces: the spacing of the fatigue surfaces from different granule types is a measure for granule strength.

Results of experiments with different sizes and different velocities for a single type of granule all lie on a well defined three dimensional curved surface. The curved surfaces illustrate that the use of compressive force and number of repetitions is a complete measure for granule fatigue. The surfaces provide a lot of information about fatigue development in the granules.

The complex analysis provided by the present invention is needed to accurately describe the damage to the three different types of granules in using compressive strength behavior.

EXAMPLE 5

The attrition rates of four different samples of multilayered granules were tested, samples 1–4. The granules consisted of a substantially spherical core containing enzyme, lactose, and sucrose. The core constituted 100 parts by weight of the mass of each granule. The granules are coated with an overcoated polymeric layer which constituted 20 parts by weight based on the weight of the core material. Thus, the total weight of each granule was 120 parts by weight and the interface between the core and the overcoat of each granule was close to the outermost surface of each granule. The interface was reached after about 20 parts by weight of each granule was worn from the outer surface of the granule.

Although the mass of the granules reported in the graph of FIG. 5 was based on 120 parts by weight constituting the entire weight of each sample, the compositions of the four samples based on a total weight of 100 parts by weight each are shown below.

Each of samples 1–4 comprised a multilayered enzyme granule having a seed, core or marume composition coated by a coating composition. The compositions of samples 1 and 2 were identical and are shown in Table 7 below. The difference between samples 1 and 2 is that the samples were derived from different batches. The composition of the sample 3 granules was substantially identical to the composition of the sample 1 and sample 2 granules with the exception that the amount of lactose in the sample 3 granules was only 0.5 parts by weight lactose instead of 4.7 parts by weight lactose as in samples 1 and 2. The composition of the sample 4 granules was identical to the composition of the sample 1 and 2 granules with the exception that the sample 4 granules contained 0 parts by weight lactose.

TABLE 7

| SAMPLE 1 AND SAMPLE 2 COMPOSITIONS | | |
| --- | --- | --- |
| Component | Type | Parts by Weight |
| MARUME COMPOSITION | | |
| Clarsol KC 2 | Bentonite | 10.4 |
| Socal P-2 | Calcium carbonate | 7.66 |
| Dorkamul 16900 | Kaolin | 4.1 |
| Arbocel 60/30 | Cellulose fiber | 15.7 |
| PVP K-90 | Polyvinylpyrrolidone | 0.7 |

TABLE 7-continued

SAMPLE 1 AND SAMPLE 2 COMPOSITIONS

| Component | Type | Parts by Weight |
|---|---|---|
| Calcium formate | | 1.4 |
| Wheat flour | | 4.7 |
| Lactose | | 4.7 |
| Netzer IS | | 0.3 |
| PEG 3000 | Polyethylene glycol | 6.9 |
| Solid from fermentation and recovery | | 20.0 |
| Total Parts by Weight Marume Composition | | 77 |
| COATING COMPOSITION | | |
| Socal U-1 | Calcium carbonate | 1.3 |
| Socal P-2 | Calcium carbonate | 6.54 |
| Kronos 2044 | $TiO_2$ | 9.4 |
| PEG 200 | Polyethylene glycol | 0.7 |
| PEG 4000 | Polyethylene glycol | 5.4 |
| Total Parts By Weight Coating Composition | | 23 |
| Total Product | | 100 |

For each of the four samples, from about 60 to about 100 granules were placed inside the testing device shown in FIGS. 1–4. The total weight of each sample tested was about 30 mg. The container had a height of about 3.0 cm, a width of about 1.8 cm, and a length of about 1.3 cm. The testing device was then vibrated at a frequency of 60 hertz and at an amplitude of 1.5 cm to provide a repeated impact to the granules within the container off of the top and bottom inner surfaces of the container. Periodically the mass of the granules during the test was measured to determine the attrition rate based on the changing mass of the granules.

Given the original mass value and the measured mass values, the attrition rate (A) was calculated from the following equation.

$$A = \Delta M / \Delta n = (M_f - M_i)/(n_f - n_i)$$

where M is the mass of the granules with 120 parts by weight being the mass of each whole sample, n is the number of collisions, and the subscripts "i" and "f" refer to initial and final, respectively, as in the initial and final mass and the initial and final number of collisions. The mass of the granules after vibration can be determined, for example, by separating undamaged granules and large damaged granules from dust, fines, small granule fragments, and small granules by sieving the vibrated granules through an appropriately sized sieve. For progressive measurements, progressively smaller sieve size openings can be, but are not necessarily, used.

Figure 5:
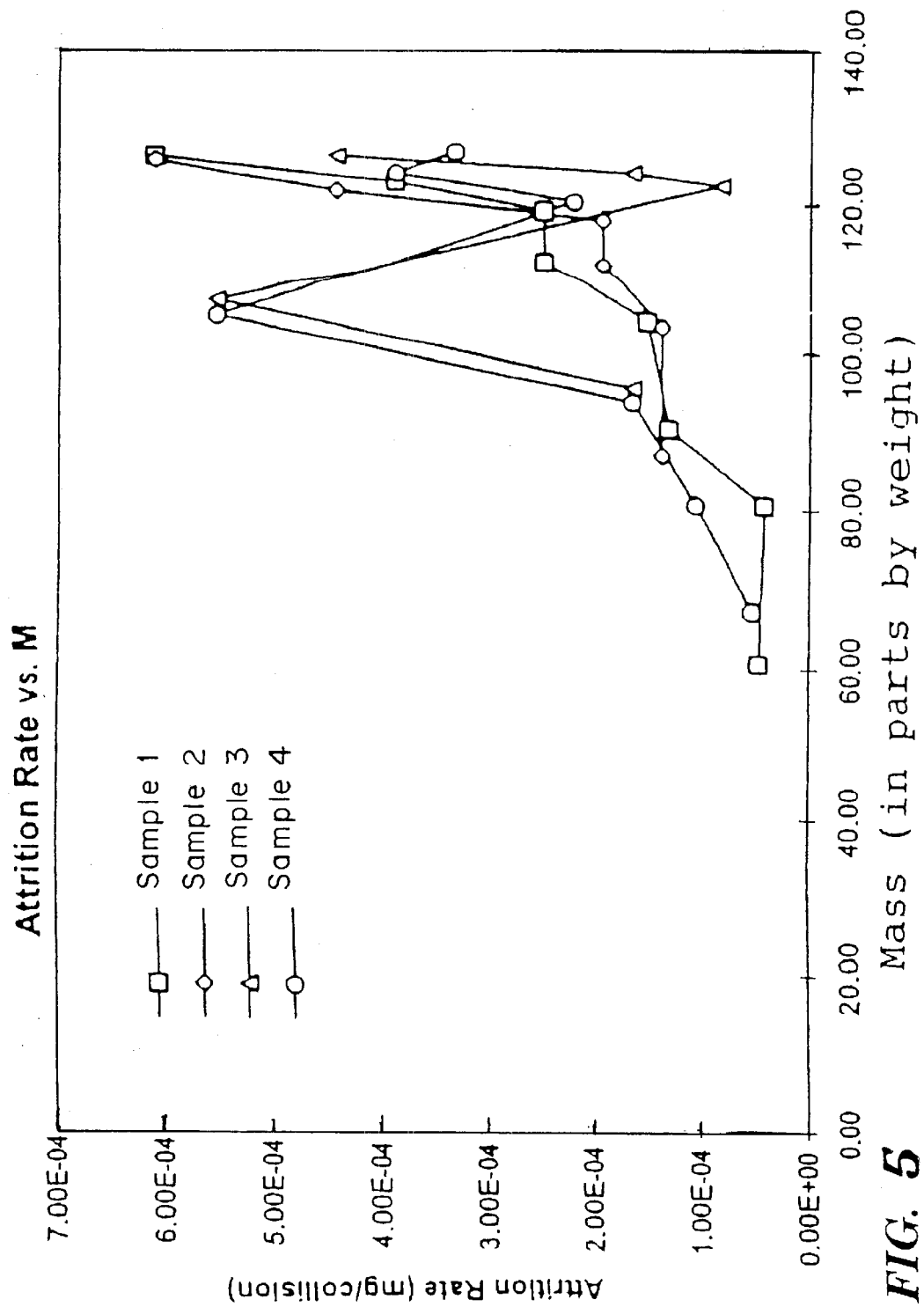
FIG. 5 is a graph showing the attrition rate of four different granule samples in terms of the rate versus the mass of the samples.

From the graph shown in FIG. 5, it can be seen that similar attrition rates were present in the four different granules tested at every point except where the mass was reduced from the original mass of 120 parts by weight to a mass of about 100 parts by weight (at about the coating interface) where the attrition rate was much higher for two of the four granules tested. As can be seen in FIG. 5, as the mass of the granules decreased as a result of wear of the polymeric overcoat layer, the attrition rate of the granules decreased dramatically. However, as the outer polymeric overcoat layer of the granules was worn and the outer surfaces of the granules approached the interface between the overcoat layer and the granule core, the attrition rate of two of the samples increased dramatically whereas the attrition rate of the other two samples did not increase. The interface between the overcoat layer and the core is shown in the graph of FIG. 5 along the X axis at the mass value (M) of 100.00. The drastic change in attrition rates between the two groups of granules is attributable, in this case, to the composition of the respective granule cores. As can be seen, the samples containing 0.5 parts by weight lactose and 0.0 parts by weight lactose (samples 3 and 4, respectively) had much higher attrition rates at the coating interface than did samples 1 and 2.

The method can be useful for characterizing the weaknesses at layer interfaces of granules as demonstrated above. In addition, the method can also be useful to evaluate attrition rates within individual layers, for example, the individual attrition rate and thus the strength of an outer coating layer, an enzyme layer, a salt or pigment matrix layer, and a core or seed can be determined by calculating an attrition rate for that individual layer or component of a granule. The results of these tests can be used in determining what compositional adjustments could be useful to strengthen the granule or one or more granule layers. Stronger particles can thus be designed by replacing weaker materials or weaker combinations of materials with stronger ones. Analysis of the breakage mechanisms involved by Fourier optics, Raman spectroscopy, fluorescence spectroscopy, or other analytical devices or methods can be used to determine properties of the granules and/or to discriminate between attrition and fracture. An aerosol sizer can also be used to discriminate between attrition and fracture. Changes in shape can be used to provide information to distinguish between attrition and fracture and can be detected using Fourier transform and performing crosscorrelation in the angle spectrum.

As demonstrated by the results presented herein, the present invention can be used for characterizing, for example and not for limitation, granulated industrial catalysts, industrial enzymes, and food enzymes. The present invention is also applicable for identifying problems and providing solutions to the use of granules in the pharmaceutical industry, the grinding of clinker in the cement industry, the creation of dust in the milling of flour and other foodstuffs, or dust generated by mining and quarrying. Another example of the present invention's applicability is with the large particle attrition which occurs with railroad ballast where properties degrade due to the motion of the sleepers causing lateral instability. A further application of the present invention is the generation of fines within packed columns used in gas-liquid chromatography which lowers efficiency and increases pressure drop.

Numerous modifications and variations of the present invention are possible in light of the above teachings. It is therefore to be understood that within the scope of the appended claims, the invention may be practiced otherwise than as specifically described herein.

What is claimed is:

1. A method of characterizing the granule strength of a granule comprising the steps of:

disposing at least one granule to be tested within a container;

repeatedly impacting the at least one granule within the container by moving the container at an amplitude such that granule damage occurs;

separating larger damaged granules and undamaged granules from dust, fines, smaller granule fragments and smaller granules, to form first separated large granules;

measuring the weight of the first separated large granules as a consequence of a number of collisions between the at least one granule and inner walls of the container;

repeatedly impacting the first separated large granules within the container by moving the container at said amplitude such that granule damage occurs;

separating larger damaged granules and undamaged granules from dust, fines, smaller granule fragments and smaller granules resulting from repeatedly impacting the first separated large granules to form second separated large granules;

measuring the weight of the second separated large granules as a consequence of a number of collisions between the first separated large granules and the inner walls of the container; and determining an attrition rate of the at least one granule.

2. The method of claim 1, wherein determining the attrition rate comprises comparing a measured mass of dust generated per number of collisions to a mass of the at least one granule as a function of the number of collisions between the at least one granule and the inner walls of the container.

3. The method of claim 1, wherein determining the attrition rate comprises comparing a rate of change in mass as a function of the number of collisions to a mass of the at least one granule.

4. The method of claim 1, wherein the granule damage substantially occurs only due to collisions between the at least one granule and the inner walls of the container.

5. The method of claim 1, wherein said at least one granule is at least one multilayered granule.

6. The method of claim 1, wherein said at least one granule is at least one enzyme-containing granule.

7. The method of claim 1, wherein said container has a top wall, a bottom wall, and at least one side wall, said top wall and said bottom wall have opposing inner surfaces, and said repeatedly impacting comprises alternately impacting the at least one granule against the inner surface of the top wall then against the inner surface of the bottom wall.

8. The method of claim 1, wherein said container is a closed container.

9. An apparatus for analyzing breakage or strength characteristics of a granular material, comprising:

a container having a top wall, a bottom wall, and one or more side walls, said container for containing one or more granules of a granular material to be tested; and a reciprocating motion device directly or indirectly in contact with said container for causing said container to move in a reciprocating motion.

10. The apparatus of claim 9, wherein said container contains at least one granule.

11. The apparatus of claim 9, wherein said reciprocating motion device causes said container to move at a first amplitude in a direction of reciprocal motion, said container having a height defined as a distance between an inner surface of said top wall and an opposing inner surface of said bottom wall, and wherein said amplitude is greater than said height.

12. The apparatus of claim 9, wherein said top wall has an inner surface and said bottom wall has an inner surface facing the inner surface of said top wall, and the inner surfaces of said top wall and said bottom wall are substantially parallel to each other.

13. The apparatus of claim 12, wherein the inner surfaces of said top wall and said bottom wall are parallel to each other.

14. The apparatus of claim 9, wherein said container contains at least one granule to be tested, said container has a height defined as a distance between an inner surface of said top wall and a facing inner surface of said bottom wall, and the height of said container is from about 5 times to about 1000 times an average diameter of said at least one granule to be tested.

15. The apparatus of claim 9, wherein said container is secured to a platform and said reciprocating motion device causes reciprocating motion of said platform.

16. The apparatus of claim 9, wherein said reciprocating motion device comprises a cam.

17. The apparatus of claim 16, further comprising a platform, a securing device to secure said container to said platform, and wherein said reciprocating motion device causes said platform to reciprocate.

18. The apparatus of claim 9, further comprising a drive shaft having a first end and an opposite second end, wherein said first end engages said reciprocating motion device and said second end engages, directly or indirectly, said container.

19. The apparatus of claim 18, further comprising a platform and a securing device to secure said container to said platform, and wherein said second end of the drive shaft engages said platform to cause reciprocating motion of said platform.

20. The apparatus of claim 9, wherein said reciprocating motion device comprises a piston.

21. The apparatus of claim 9, wherein said reciprocating motion device comprises a piston-operated engine, motor, or pump.

22. The apparatus of claim 21, wherein said reciprocating motion device comprises a pneumatic-or electric-powered piston.

23. The apparatus of claim 9, wherein at least one of said top wall, said bottom wall, and said one or more side walls is removable and replaceable for enabling access to an interior of said container.

24. The apparatus of claim 9, wherein said reciprocating motion device comprises a rotating drive axle having an axis of rotation, a drive wheel connected to said drive axle, said drive wheel having an axis of rotation wherein said drive axle rotates said drive wheel about said drive wheel axis of rotation, a drive shaft connected at a first end, directly or indirectly, to said container, and wherein said drive shaft is connected at a second end opposite said first end to said drive wheel at a location offset from the axis of rotation of said drive wheel.

25. The apparatus of claim 9, wherein said reciprocating motion device comprises a variable speed motor for providing a variable speed reciprocating motion.

26. A method of characterizing the granule strength of a granule comprising providing the apparatus of claim 9, placing at least one granule to be tested in said container, reciprocating the reciprocating motion device, and measuring attrition of the at least one granule after said reciprocating.

27. An apparatus for analyzing breakage or strength characteristics of a granular material, comprising:

container means having a top wall, a bottom wall, and one or more side walls, said container means for containing one or more granules of a granular material to be tested; and a reciprocating motion means directly or indirectly in contact with said container means for causing said container means to move in a reciprocating motion.

* * * * *